United States Patent
Richardson et al.

[11] Patent Number: 5,951,549
[45] Date of Patent: Sep. 14, 1999

[54] BIPOLAR ELECTROSURGICAL SCISSORS

[75] Inventors: Theodore A. Richardson; Matthew J. Winkler; Michael D. Hooven, all of Cincinnati, Ohio

[73] Assignee: Enable Medical Corporation, West Chester, Ohio

[21] Appl. No.: 08/771,231

[22] Filed: Dec. 20, 1996

[51] Int. Cl.$^6$ .................................................. A61B 17/36
[52] U.S. Cl. ............................... 606/45; 606/48; 606/50
[58] Field of Search .................... 606/45, 48, 42, 606/51, 52, 208, 206, 207, 174

[56] References Cited

U.S. PATENT DOCUMENTS

| | | | |
|---|---|---|---|
| 2,725,628 | 10/1955 | Todhunter | 606/174 |
| 4,041,952 | 8/1977 | Morrison | 128/303.13 |
| 4,161,950 | 7/1979 | Doss et al. | 128/303.14 |
| 5,157,837 | 10/1992 | Rose . | |
| 5,514,134 | 5/1996 | Rydell et al. | 606/50 |
| 5,540,685 | 7/1996 | Partins et al. | 606/51 |
| 5,569,243 | 10/1996 | Kortenbach et al. | 606/46 |
| 5,618,303 | 4/1997 | Marlow et al. | 606/205 |
| 5,658,281 | 8/1997 | Heard | 606/48 |
| 5,665,085 | 9/1997 | Nardella | 606/41 |
| 5,893,875 | 4/1999 | O'Connor et al. | 606/205 |

*Primary Examiner*—Brian L. Casler
*Attorney, Agent, or Firm*—Cook, McFarron & Manzo, Ltd.

[57] ABSTRACT

An electrosurgical instrument, such as a scissors, in which the handle and blade members are of a conventional construction. Each blade member supports a detachable cartridge member made of an insulating material and supporting at least one electrode. The cartridge members do not interfere with the cutting engagement of the blade members. Each cartridge member can also permit relative movement between its electrode and associated cutting edge from a first position in which the electrodes are between the cutting edges (when the blades are open) to a second position in which each electrode is behind its respective cutting edge (as the blades are closed).

32 Claims, 10 Drawing Sheets

BIPOLAR ELECTROSURGICAL SCISSORS

The present invention relates generally to electrosurgical scissors, and more particularly to bipolar electrosurgical scissors to assist in the hemostasis of tissue as it is cut by the scissors.

BACKGROUND OF THE INVENTION

Surgical scissors are commonly used in many surgical procedures for cutting tissue that is vascularized, i.e., contains blood or other vessels. The resultant bleeding or other fluid loss that occurs is not only of concern from the standpoint of fluid loss, but blood may also obscure the surgical field or site. Controlling such fluid loss and bleeding has, in the past, required significant time and attention of the surgeon during many surgical procedures.

Scissors that use radiofrequency (RF) energy in a manner such that the tissue is heated as it is cut, thus promoting immediate hemostasis, have been used for many years to control such bleeding or other fluid loss. Early electrosurgical scissors used monopolar RF power, where the scissors constituted one electrode and the patient rested on the other electrode (which was typically in the form of a conductive mat) to complete the circuit. Current flowed generally through the patient between the electrodes due to the voltage applied across the electrodes by an RF power supply. The uncertainty of the path of current flow through the body and possible unintentional harm to other tissues, however, encouraged the further development in electrosurgical scissors.

Recently, efforts have been made to develop electrosurgical scissors, as illustrated, for example, in U.S. Pat. Nos. 5,324,289 and 5,330,471, in which one blade includes one electrode and the other blade includes or functions as the other electrode, so that current flows between the blades as they cut the desired tissue.

More recently, electrosurgical scissors have been provided in which each cutting blade itself includes two electrodes for connection to a RF energy power supply. The tissue contacting surfaces of at least one, and preferably both, blades include two spaced-apart electrodes which extend along the tissue contacting surface and are connectable to a voltage source for applying a voltage between the electrodes of each blade. As a result, current flows between the first and second electrodes of each blade to promote hemostasis in the tissue as the blade is moved into contact with the tissue, such as during the cutting action. Such scissors are disclosed in the co-pending applications Ser. No. 399,421 filed Mar. 7, 1995 and Ser. No. 593,148, filed Feb. 21, 1996, which are herein incorporated by reference. Another example of electrosurgical scissors is also disclosed in U.S. Pat. No. 5,540,685.

Although electrosurgical scissors have generally performed well in promoting hemostasis, need for further improvement to enhance their long term use has become evident. Specifically, the cutting edges of the scissor blades typically dull after repeated use, and require resharpening. The presence of one or more electrodes and insulators on a blade, however, significantly complicates and increases the expense and/or time for resharpening of the scissors blades. Further, as with all reusable medical instruments, there is a need to provide for easy re-sterilization of the instrument between uses. The presence of an electrode and insulation structure on the blade or blades can make thorough cleaning and sterilization more tedious and time consuming. Finally, repeated use of steam sterilization can result in undesirable wear or breakdown of the electrodes and their associated insulating material, necessitating more frequent replacement than might otherwise be required for standard, non-electrosurgical scissors.

Accordingly, there is a continuing need for electrosurgical scissors which are reusable, more easily resharpened and resterilized, and providing longer product life.

SUMMARY OF THE INVENTION

In accordance with the present invention electrosurgical scissors may be provided in which the blade members are of generally conventional construction and include a shearing face and a cutting edge. As with conventional surgical scissors, the blades may be made of standard stainless steel or other suitable material, which is typically an electrically conductive material, and the blades are pivotally connected, with their shearing faces facing one another.

In accordance with one aspect of the present invention, at least one blade carries a detachable cartridge member. The cartridge member includes a tissue engaging surface disposed, when mounted on a blade, to engage the tissue being cut as the scissor blades close on the tissue, but without interfering with the cutting engagement of the blade members. The cartridge member includes at least one electrode on the tissue engaging surface, which electrode is insulated from the electrically conductive material of the blade on which it is mounted so as not to cause a short circuit when tissue is not engaged.

In electrosurgical scissors employing the present invention and using a cartridge member of the present invention on only one blade, the supporting and/or opposing blade member(s) may function as or include the opposing electrode. In such an embodiment, the electrode on the cartridge member is preferably of one polarity and the shearing surface, cutting edge and/or other tissue contacting surface of one or both of the scissors blades are of electrically conductive material and of the opposite polarity. As a result, as the blades contact tissue being cut, electrical current flows through the tissue between the electrode of the cartridge member and the cutting edge, shearing surface or other tissue contacting surface of the same and/or opposing blade to promote coagulation as the blades cut the tissue. As used herein, reference to electrodes of "opposite polarity" includes electrodes, blades or blade surfaces that are connected (or connectable) to opposite terminals of what are commonly called the bipolar terminals of a radiofrequency ("RF") generator or connected (or connectable) to what are commonly called the monopolar active and return terminals of an RF generator, although it is expected that bipolar connection will be preferred.

In accordance with another and preferred embodiment of the present invention, each blade of the scissors removably carries a cartridge member of the present invention, which cartridge includes at least one electrode on the tissue engaging surface. The electrodes of the cartridge members are connectable in common to one terminal of a RF generator and the shearing surfaces and/or cutting edges of the blades are of electrically conductive material and connectable in common to an opposite terminal of the RF generator to form electrodes of opposite polarity to the cartridge member electrodes.

In the above described embodiments, the electrode on the cartridge member may be elongated and extend generally parallel to the cutting edge of the blade on which it is carried to provide electrical contact along the tissue as it is cut. One or both of the blade members may also include a tissue contacting surface of electrically conductive material that extends generally parallel to the cutting edge and is of opposite polarity to the electrode of the cartridge member. When the cartridge is carried by a blade member having such a tissue contacting surface, the tissue contacting surface of the cartridge member may be substantially parallel to and coplanar with the tissue contacting surface of the blade member to provide for current flow therebetween as the tissue contacting surfaces are brought into contact with tissue as the blades close. Preferably the electrode is in a relatively raised position, which provides earlier contact with the tissue and increased surface area of the electrode for greater contact with the tissue.

In accordance with other aspects of the present invention, the cartridge member may include a plurality of electrodes. For example, each cartridge member may include a pair of electrodes in electrical communication so as to be of the same polarity.

In a further alternative, the cartridge member may include two electrodes on the tissue contacting surface, which electrodes are electrically insulated from one another and from the blade member on which the cartridge is carried. The electrodes in this alternative are adapted for connection with opposite terminals of an RF energy power supply so that current flows between the electrodes through the tissue contacted as the blades close during the cutting action.

In yet a further embodiment of the present invention, the electrode is movable relative to the blade member on which it is carried. In this embodiment, the electrode is movable, such as by shifting or flexing of the cartridge, between a first position (when the blade members are open) in which the electrode is located between the cutting edges of the blade members and a second position in which the electrode is located substantially parallel to or behind the cutting edge of the respective blade member (when the blade members are closed on tissue to be cut) so as not to interfere with the cutting action of the blade members. The movement of the electrode is preferably effected by engagement of the tissue engaging surface of the cartridge (which carries the electrode) against the tissue between the scissor blade members as the blade members close. Pressure by the tissue as the blades close causes the cartridge member to shift or flex, allowing the electrode to move from the first position to the second position.

A further aspect of the present invention is the cartridge member itself. In accordance with this aspect, a cartridge may be provided for removable attachment to the blade of surgical scissors to provide multiple electrode electrosurgical capability to scissors which otherwise function as standard non-electrosurgical scissors or monopolar surgical scissors. The cartridge may include a base portion attachable to a scissors blade and at least one electrode carried on the base portion. The cartridge includes a tissue contacting surface disposed so that when the cartridge is mounted on a scissor blade, the electrode associated with the tissue contacting surface will contact the tissue being cut as the scissor blades close on it. The electrode defines at least a portion of the tissue contacting surface of said cartridge and the base portion comprises an electrically insulative material for insulating the electrode from the blade of a scissors when mounted thereon.

As described above, the cartridge may include a plurality of electrodes that are in electrical communication or are electrically insulated from one another, and the electrode(s) may be elongated and parallel, if so desired. The elongated electrode(s) may have a proximal contact portion for contacting an electrical conductor associated with the scissors, an intermediate elongated portion that lies along the tissue contacting surface and a distal nose portion for fitting over the distal end of the base portion. The electrode may also include a tissue gripping surface, such as a sawtooth profile, along the intermediate portion to better assure contact with the tissue between the blades.

The cartridge base portion is preferably made essentially entirely of electrically insulative and resilient material which resist tissue sticking, such as nylon, ABS, flouropolymer, or the like, and includes interfitting projections or recesses for interference fit with corresponding recesses or projections on a scissors blade.

These and other features and advantages of the present invention are set forth in more detail in the accompanying drawings and the following detailed description of these drawings.

DETAILED DESCRIPTION OF THE DRAWINGS

Figure 1:
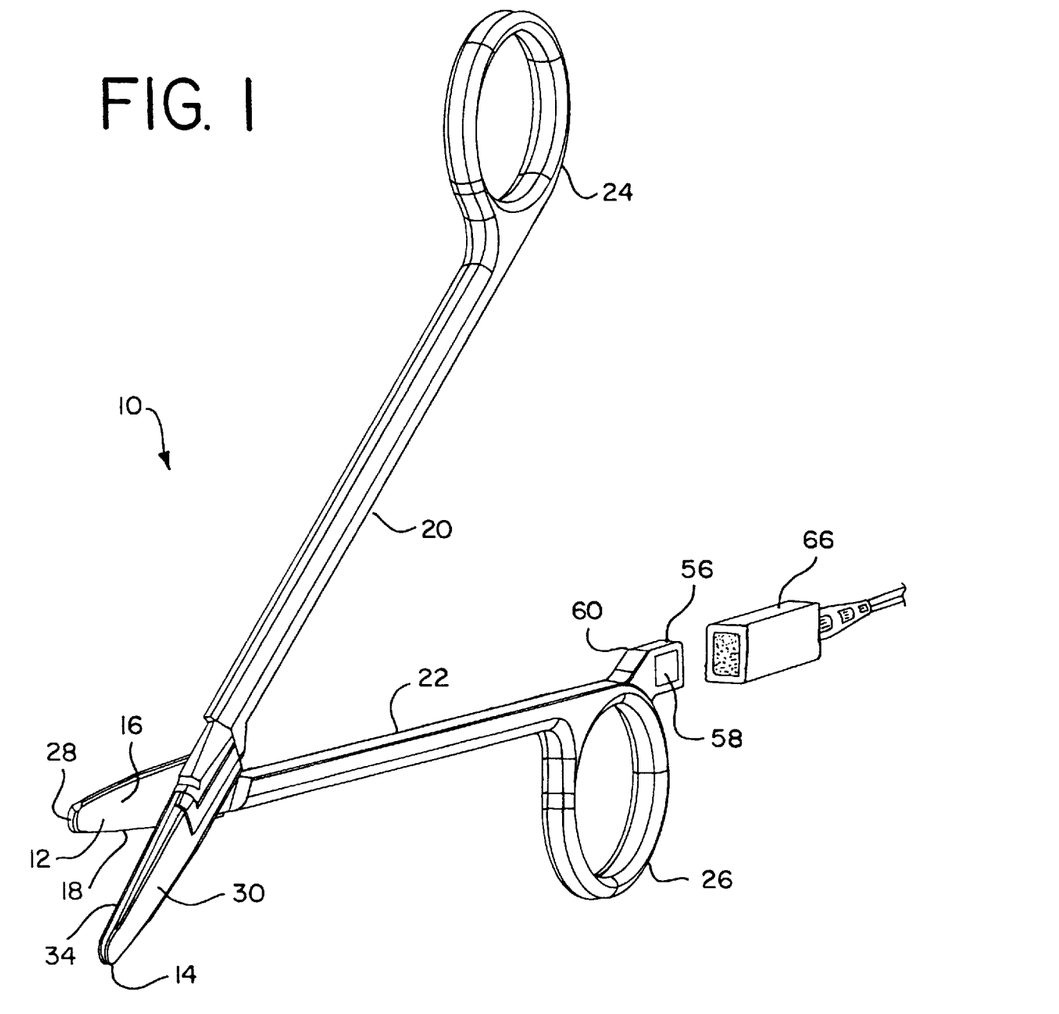
FIG. 1 is a perspective view showing an electrosurgical scissors embodying the present invention.
Figure 2:
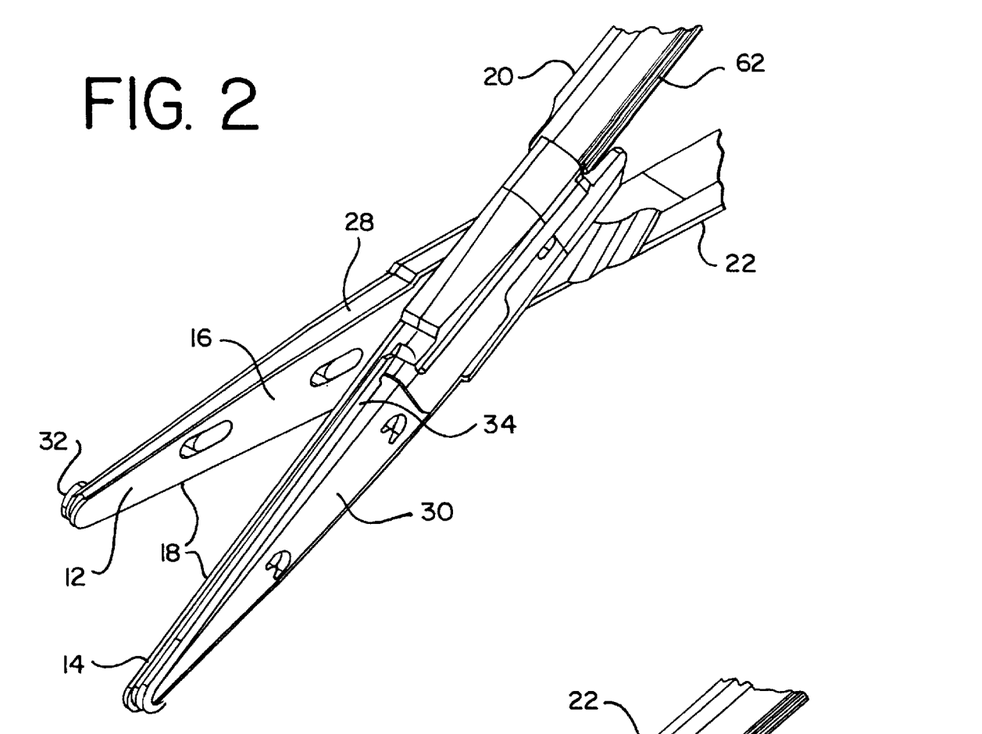
FIG. 2 is an enlarged perspective view of the blade portion of the electrosurgical scissors of FIG. 1 with the cartridge members attached and the blades in the open position.

Turning to FIGS. 1 and 2, the present invention is generally embodied in an electrosurgical scissors, generally indicated by 10, having a pair of blade members 12, 14 each having a shearing surface 16 that terminates in a cutting edge 18. The blade members are joined for pivotal movement, with the shearing surfaces 16 facing one another, between open and closed positions. As illustrated, the scissors 10 are for an open surgical procedure, and each blade member 12, 14 has a handle member 20, 22 associated therewith. Each handle 20, 22 terminates in a ring 24, 26 through which the user's finger and thumb fit to move the scissor blades 12 and 14 between their open and closed positions.

As thus far described, the scissors 10 are of conventional configuration and construction. Although the scissors shown are for so-called open surgical procedures, the present invention is not limited to such applications and may be employed in scissors of the type used in minimally invasive surgery or other non-open surgical procedures. Such scissors typically have an elongated barrel with actuating rods, actuated by a trigger, extending through the barrel and operably connected to pivot one or both blades in a scissor-like cutting action. One example of such a scissors is found in the above-identified co-pending applications. Other examples are found in the cited U.S. Pat. Nos. 5,324,289 and 5,330,471.

Similarly, the present invention is useful in scissors in which both blade elements pivot or in which one blade element is fixed and the other pivots to cause a relative pivoting between the blades. The above structures are well known in electrosurgical scissor field, and the present invention may find application in any of these scissors and is not limited to a particular type or style of scissors.

In keeping with the present invention, at least one electrode is associated with at least one and preferably each blade 12, 14 so that the electrode is removable and disposable, while the scissors are reusable. To this end, a preferably disposable cartridge member 28, 30, each supporting an electrode 32, 34, respectively, is removably supported by each blade 12, 14.

Figure 5A:
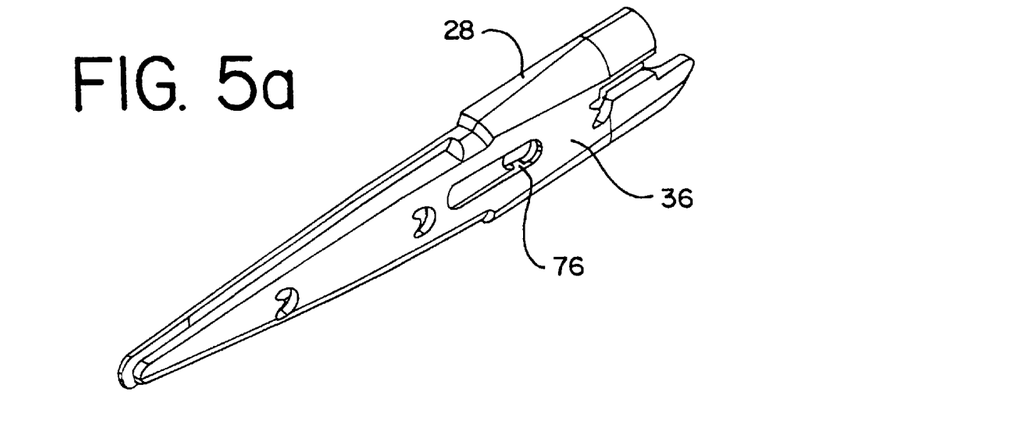
FIGS. 5a–c are enlarged perspective views of a single cartridge member base portion of the electrosurgical scissors of FIG. 2.
Figure 5B:
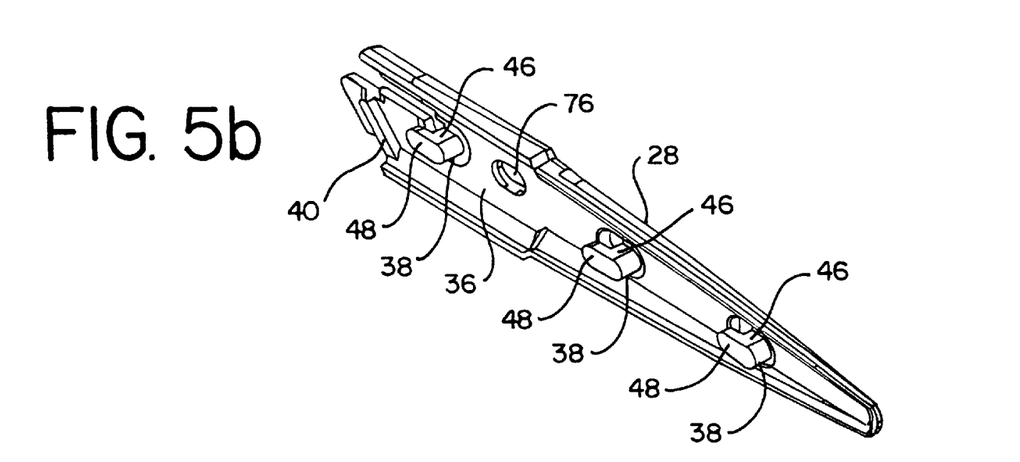
Figure 5C:
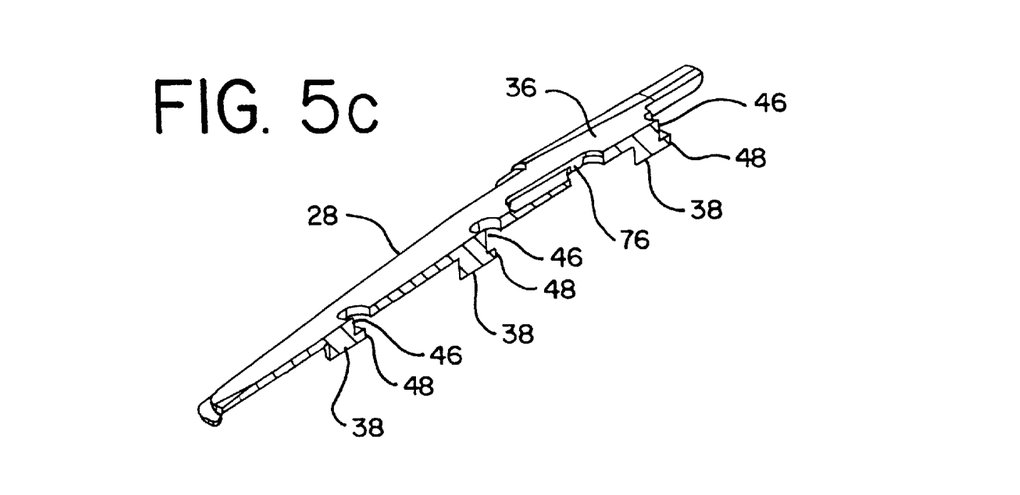

As better seen in FIGS. 5a–c, cartridge member 28 preferably has a base portion 36, of insulative material, upon which electrode 32 is carried. (While FIGS. 5a–c illustrate only a single cartridge member 28, it should be understood that the characteristics of cartridge member 30 and its associated electrode 34, are the same as cartridge member 28 and its associated electrode 32.) The base portion of the cartridge member 28 is preferably made of a compressible or flexible insulating material which resists tissue sticking and buildup of coagulants, such as nylon, ABS, epoxy or Teflon, although other high dielectric, high temperature thermoplastics may be used. Hivalloy GXPA062 glass reinforced resin manufactured by Montell Polyolefins has been found to be a suitable cartridge material. The electrodes 32, 34 can be made of a stamped stainless steel or other suitable conductive material and bonded, insert molded or otherwise mechanically attached to the base portion of the cartridge.

Figures 4A, 4B:
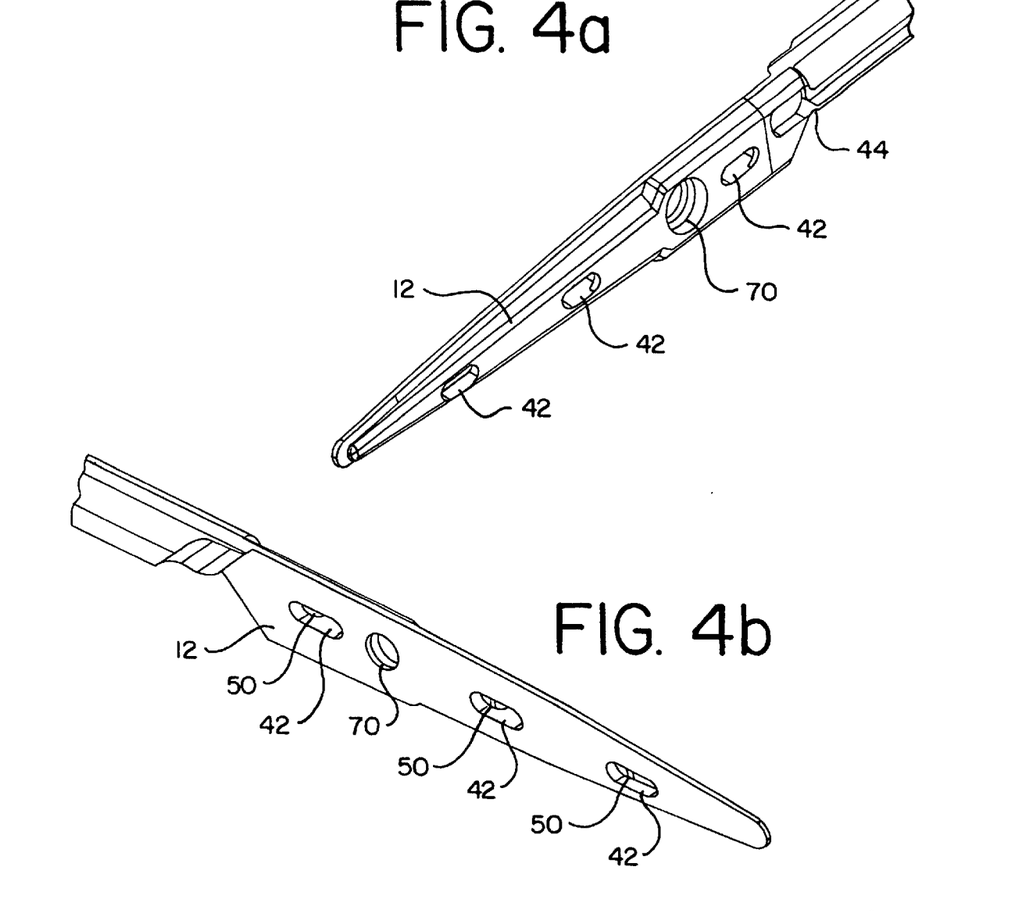
FIGS. 4a–c are enlarged perspective views of a single blade portion of the electrosurgical scissors of FIG. 2.

Again referring to FIGS. 5a–c, the base portion of each cartridge member is elongated and of similar overall size shape as the scissor blade 12 (FIGS. 4a–c) on which it is to be mounted. The base member is generally coextensive with the blade in order to substantially overlie and cover the outer surface of the blade. The cartridge 28 is secured to its respective blade member 12 through a series of pin members 38 and detent or catch 40 on the cartridge 28 (FIG. 5b) that mate with respective keyhole slots 42 and mating catch 44 on the blade member 12 (FIG. 4a).

The pin members 38 may be molded simultaneously with the cartridge or manufactured separately and subsequently bonded to the cartridge. Each pin member 38 includes a shank portion 46 with a flange portion 48 at its end that overhangs or extends beyond the shank portion 46. A detent or catch 40 (FIG. 5b) is molded into the underside of the cartridge 28 at its proximal end.

Figure 4C:
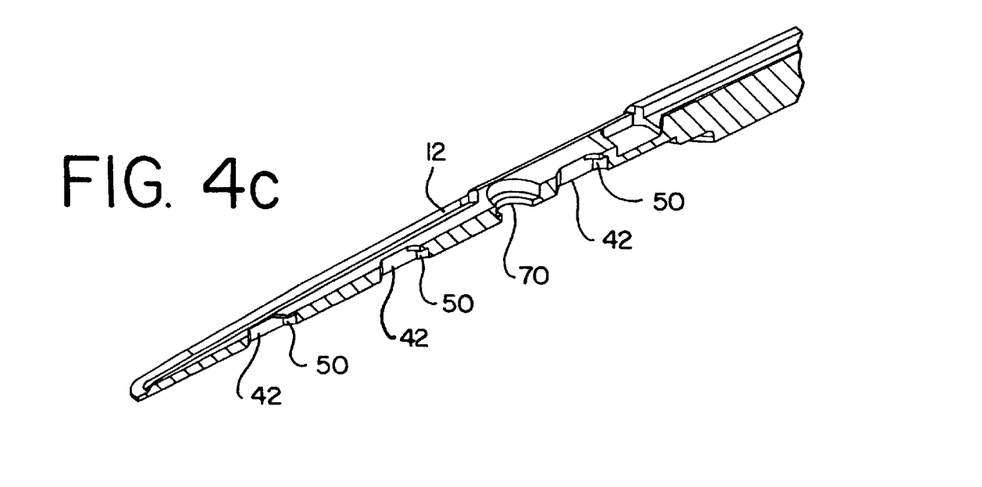

As best seen in FIG. 4c, the blade member 12 includes a keyhole slot 42 for each pin member on the cartridge. The keyhole slots 42 have the same shape as the flange portion 48 of the pin members 38 and are sized so that the flange portions 48 on the cartridge can be pushed in unison through the slots 42 on their blade member 12. Thus, once the pin members 38 are pushed through their corresponding keyhole slots 42, the shank portions can slide along the slots. When the flange portions 48 of the pins 38 engage the overhanging shoulder portions 50 of the slots 42, the detent 40 simultaneously engages the mating catch 44 on the blade member 12 to secure the cartridge 28 in place. As can be readily appreciated, the cartridges may be easily removed by applying lifting and sliding pressure to the cartridges relative to their blade members along the direction of the slots to disengage the detent 40 and the flange portions 48 of the pins 38 from the shoulder portions 50 of the slots 42, thus permitting the cartridges to be lifted away from their respective blade members.

As illustrated, in FIGS. 1 and 2 the electrodes 32, 34 are of the same polarity and the blade members 12, 14 are of the same polarity, but opposite to that of the electrodes. As shown in FIGS. 2, 6a–c each electrode has an elongated electrode surface portion 52, which lies along or adjacent to the cutting edge of the blade so as to contact tissue as the blades are closed, and a base or contact portion 54 which serves to help attach the electrode to the insulative base portion of the cartridge and to make the necessary electrical contact with electrically active terminals for transmitting voltage or energy from an RF generator to the electrodes. To enhance tissue coagulation edge 53 of the electrode surface preferably projects above the rest of the tissue contacting surface of the cartridge or the blade when it is attached. Preferably, the edge projects approximately 0.005 to 0.020 inches above the surface to provide improved tissue contact and coagulation as the scissors close, as may be better seen in FIG. 9.

Referring back to FIG. 1, in order to conduct current to the blade members 12, 14 and electrodes 32, 34, the scissors handle 22 includes a bipolar connector extension 56 having conductors 58, 60 on its opposite faces. A current pathway is provided between the connector extension 56 and the electrodes 32, 34 by means of an insulated conductive strip, such as a nylon encapsulated wire 62 (best seen in FIG. 3), which lies in a slot in the handle 22 that extends from the conductor 60 on the bipolar connector extension 56 to a cartridge contact tab 64 at the base of the blade member 12. (The handle members 20, 22 incorporate nylon insulation along their lengths. Thus, in FIG. 3, the insulation is removed from the handle member 22 to permit view of the conductive strip 62.)

Current is transmitted to the connector extension 56 through a disconnectable bipolar wire connector 66 (FIG. 1), which facilitates connection of the scissors 10 to a typical bipolar RF generator of known type (not shown). Thus, an electrical pathway is established from the bipolar electrode conductor 60 to the electrode 32, through the conductive strip 62 to the cartridge contact tab 64 at the base of the blade member 12. The cartridge contact tab 64 in turn contacts the curved end 55 on the electrode 32 to transmit current of one polarity to the electrode 32. The current is simultaneously transmitted to the electrode 34 through a connecting pivot pin, as will be described below. Current of the opposite polarity is conducted to the blade member 12 directly through the handle member 22 from the conductor 58 on the connector extension 56. Blade member 14 is, in turn, energized because its shearing surface contacts the shearing surface of blade member 12, and due to a conductive pivot screw 68 connecting the blades to each other.

Figure 3:
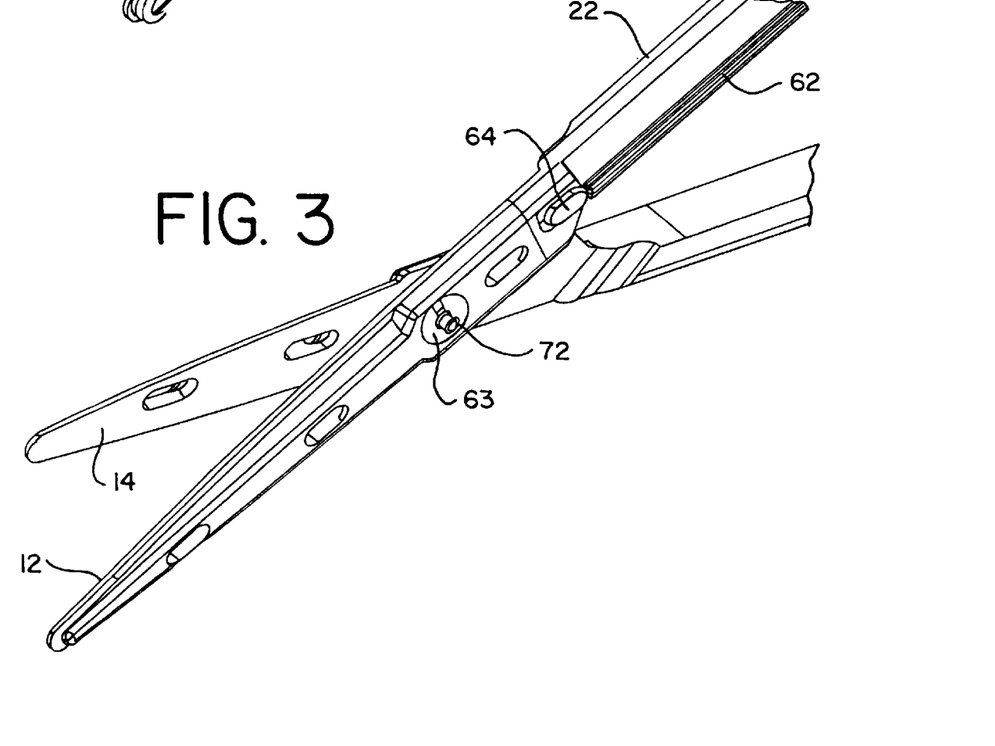
FIG. 3 is an enlarged perspective view of the blade portion of the electrosurgical scissors of FIG. 2 without the cartridge members.
Figure 6A:
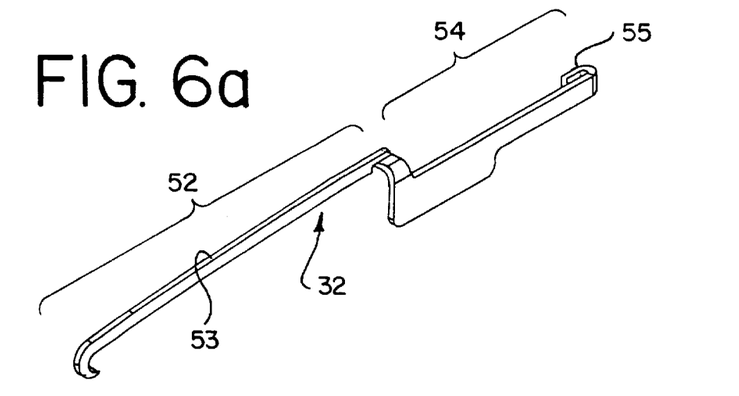
FIGS. 6a–c are enlarged perspective views of an electrode for use with the cartridge member of FIGS. 5a–c.
Figure 6B:
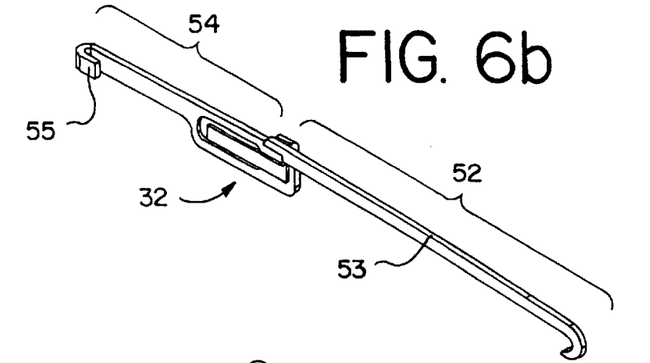
Figures 6C, 7:
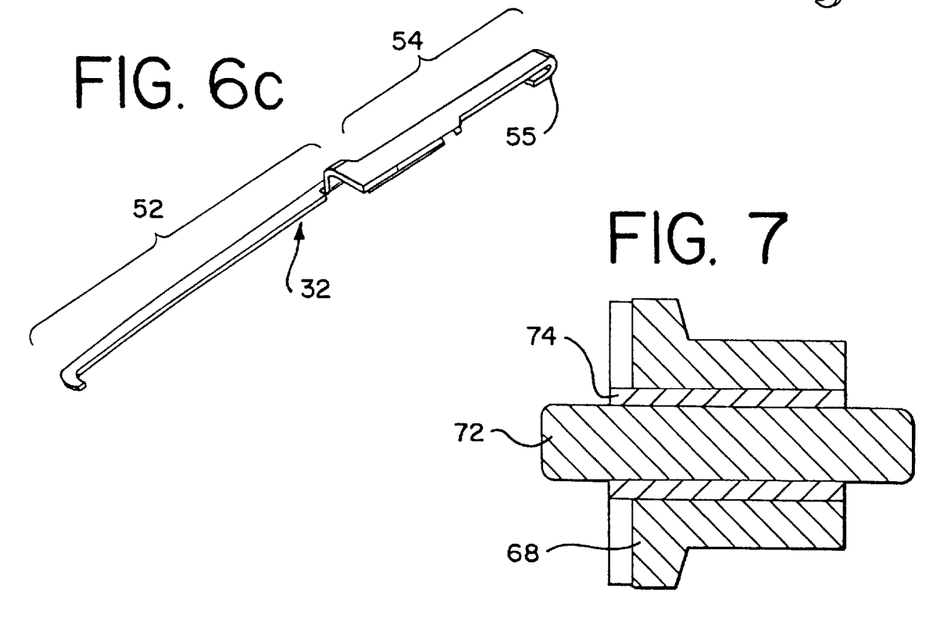
FIG. 7 is a cross-sectional view of pivot screw/current feed through pin for use with the electrosurgical scissors of FIG. 2.

In order to conduct current from the electrode 32 to the electrode 34, the blade members 12, 14 are pivotly secured to each other with a screw 68 incorporating a current feed through pin 72 that is insulated from the blade members. As best seen in FIGS. 3, 4a and 7, a screw member 68 secures the two blade members 12, 14 together through the pivot hole 70 (FIG. 4a) in the blade members 12, 14. A conductive stainless steel feed-through pin 72, which is surrounded by an insulator insert 74, is received in a central bore through the screw 68. The ends of the feed through pin 72 extend through slots 76 (FIGS. 5a–c) in the base portion of cartridges 28, 30 to contact the contact portion 54 on each of the electrodes 32, 34. Thus, current is transmitted from the conductor 60, to the electrode 32 and through the pin 72 to the electrode 34. Because the feed-through pin 72 is at the pivot point of the scissors, pivoting of the scissor blades does not affect the contact, as the pin 72 undergoes rotational, and not linear motion, relative to the cartridge electrodes.

Figure 8:
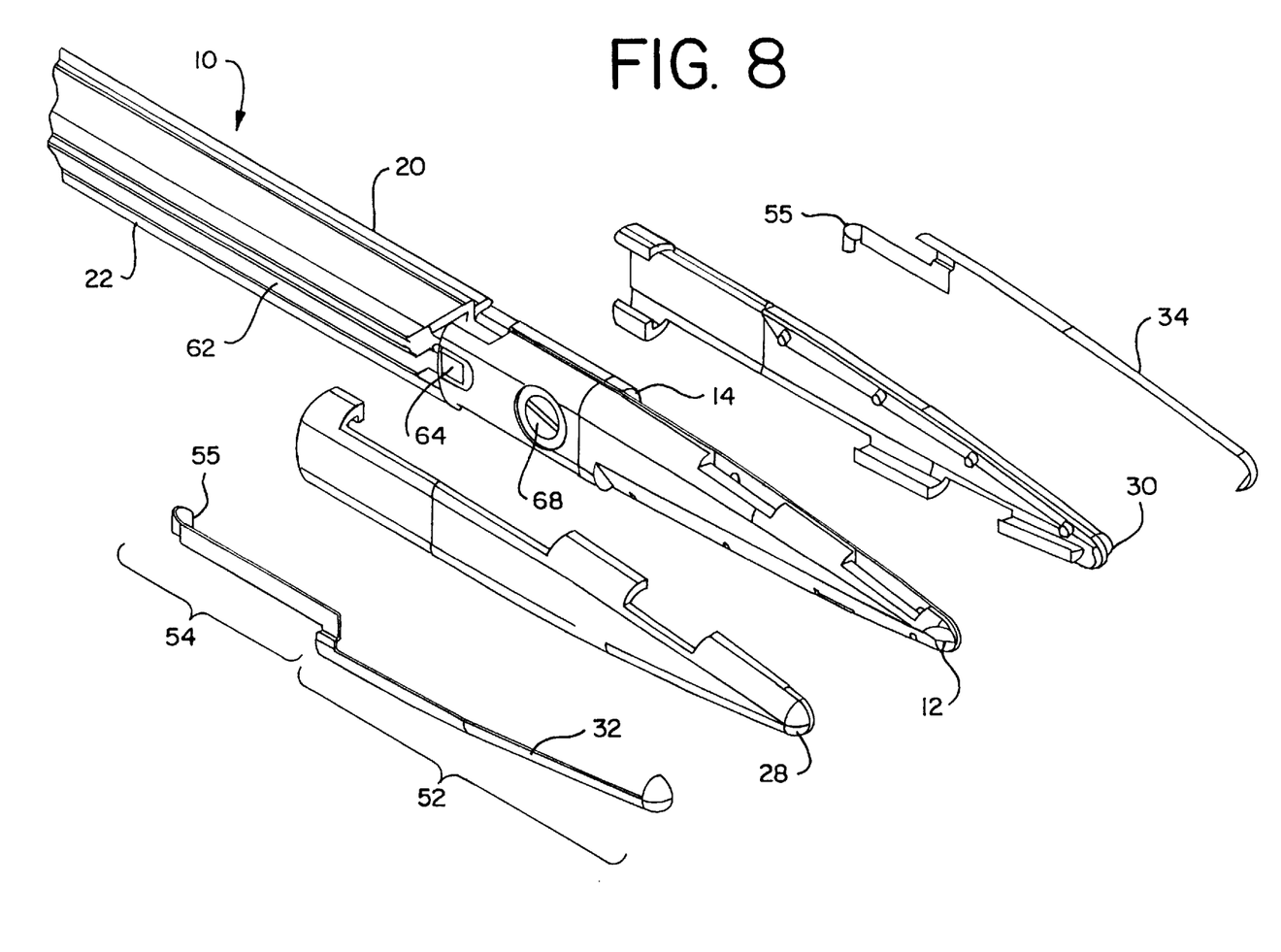
FIG. 8 is an exploded perspective view of the blade portions of an alternate embodiment of the electrosurgical scissors of the present invention with the blades in the closed position and showing the cartridge member and electrode associated with each blade.

In an alternate embodiment, illustrated in FIG. 8, the electrodes 32, 34 are of the opposite polarity, while the blade members 12, 14 are neutral or passive. Each handle member 20, 22 includes a conductor (such as conductor 58 or 60) and a nylon encapsulated wire (such as wire 62) terminating in a cartridge contact tab 64 at the base of its respective blade member. Each electrode 32, 34 includes a looped contact portion 55 that make contact with contact tab 64 to transmit current to the electrode. The electrodes 32, 34 are insulated both from each other (as the pivot connection no longer utilizes a current feed through pin) and from the blade members.

Figure 9A:
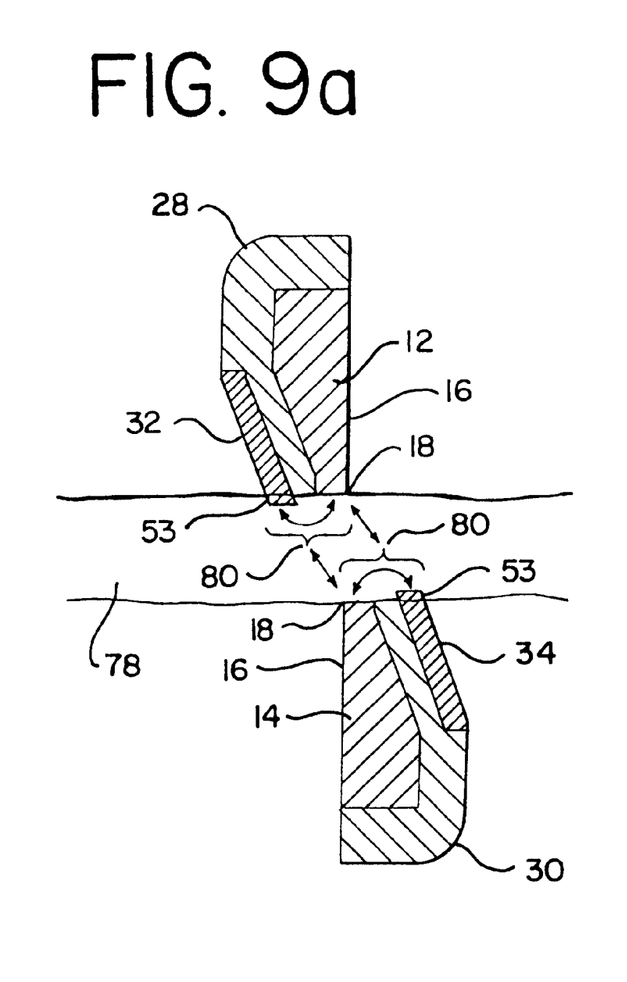
FIGS. 9a–b are cross-sectional views of a pair of bipolar electrosurgical scissor blades embodying the present invention showing the blades in an open position before the cutting of tissue (FIG. 9a) and after the tissue is cut (FIG. 9b).
Figure 9B:
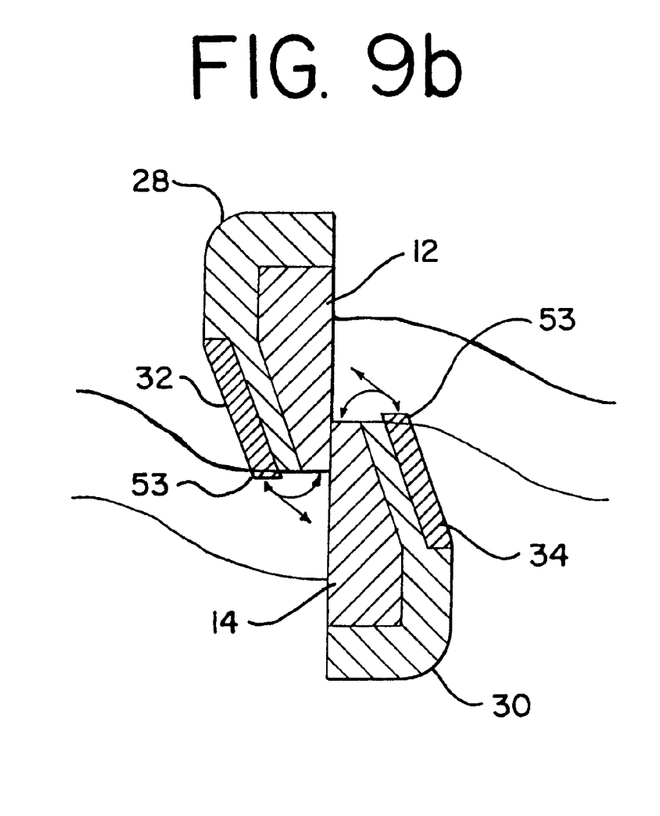

Referring to FIGS. 9a–b, FIG. 9a depicts a cross-section of the scissors of FIGS. 1–7 as they are closing and first come into contact with the tissue 78 to be severed. Each blade 12, 14 has a shearing surface 16 and a cutting edge 18. The outer surfaces and back edges of the blade members 12, 14 are covered by their respective insulative cartridges 28, 30. The electrodes 32, 34 extend along the tissue contacting surfaces of the blades and project above the surface as described earlier for enhanced tissue contact and coagulation. As shown by the arrows 80 in FIG. 9a, when the tissue contacting surfaces of the blades come into contact with the tissue 78 to be cut, current is believed to flow through the tissue between each blade member and its associated electrode. As the blades come into proximity with each other, current flows through the tissue between the blade members and the electrodes associated with the opposite blade member.

FIG. 9b shows the blades in a position where the tissue has been severed, but the blades are not fully closed. In this position, current flows substantially between the blade members and their associated electrode along the tissue contacting surfaces of the blades and between the electrodes and the shearing surfaces of the opposite blade member. The extent of current flow in this situation may vary depending on the tissue type, position, thickness, liquid content, and the extent to which the tissue is under tension.

The use of disposable cartridges as disclosed above allows the use of scissors of essentially standard construction, which can be more easily and completely cleaned, resterilized and resharpened after removal of the cartridges. Additionally, because the cartridges will be used for one procedure and then disposed of, wear and breakdown of the insulator or electrode is not a concern. Consequently, the cartridge can be made less expensively than a reusable system, since the materials do not have to survive multiple sterilization cycles.

In keeping with another feature of the invention, the cartridge member is constructed so it permits limited relative movement between the electrode of the cartridge member and its associated blade member upon contacting and cutting of tissue. This may be accomplished by making the cartridge members of a flexible material, such as Teflon, nylon or other relatively elastic material or by constructing the means that secure the cartridge members to their respective blades in such a manner so as to allow relative movement between the two. This permits compression of the tissue prior to (and during) the cutting of the tissue. The compression or "coaptation" of the tissue prior to being cut is believed to result in superior hemostasis when transecting vascular tissue, as it is well known at the sealing of vessels using bipolar energy is enhanced by compression of the tissue during energy delivery. FIGS. 10–16 show various types of movable cartridges with various electrode configurations. It should be noted that such electrode configuration are not limited to movable cartridge members, but could also be incorporated in cartridges and scissors depicted in FIGS. 1–9, with suitable conductors provided in a manner that would be readily apparent to a person skilled in the field in view of this description.

Figure 10A:
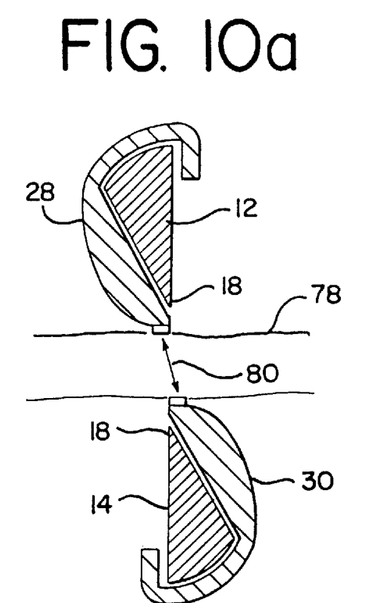
FIGS. 10a–c are cross-sectional views of a pair of bipolar electrosurgical scissor blades of an alternate embodiment of the present invention, showing the blades in an open position before the cutting of tissue (FIG. 10a), during the cutting of tissue (FIG. 10b), and after the tissue is cut (FIG. 10c).

With reference to FIGS. 10a–c, a cartridge/electrode arrangement of the type shown in FIG. 8 is shown. The cartridge members 28, 30 are configured so that when the blades 12, 14 are open prior to the cutting of tissue 78 (FIG. 10a), the cartridges 28, 30 maintain electrodes 32, 34 between the cutting edges 18 of the blade members. This causes the cartridge electrodes to first contact and compress the tissue 78 and transmit bipolar RF energy 80 through the tissue 78, between the electrodes prior to the tissue being cut (FIG. 10a). This flow of current continues as the blades close, compressing tissue between the electrodes, before cutting begins.

As the scissor blades 12, 14 close (FIG. 10b), pressure increases on the cartridges 28, 30 and their electrodes 32, 34 move toward and then away from the cutting edges 18 of their respective blade members to a retracted position, thus allowing the cutting edges 18 of the blade members to contact the tissue 78. The blade members 12, 14, which are electrically neutral, now also act as passive conductors to allow bipolar RF energy 82 to simultaneously flow from the electrodes 32, 34 on each cartridge through the tissue 78 and to the electrode's associated blade, in addition to the current flow 80 between the electrodes 32, 34.

As the blade members completely cut through the tissue (FIG. 10c), the shearing surfaces 16 of the blade members 12, 14 slide across each other and bipolar electrical current 84 flows directly from the electrodes on cartridge members through the tissue 78 to the opposite blade member, thus cauterizing tissue that is directly in contact with the blades.

Figure 10B:
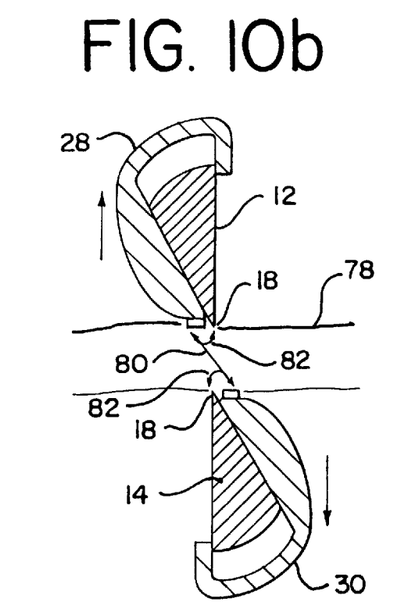
Figure 10C:
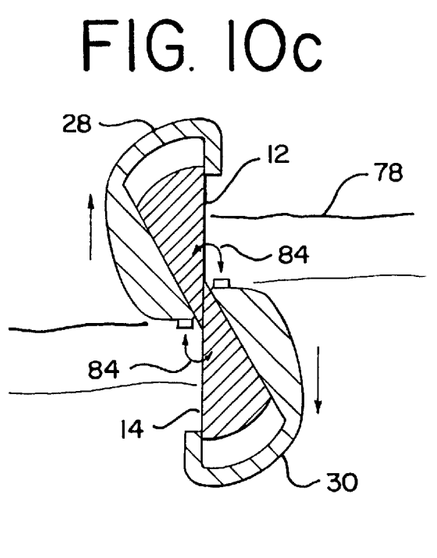
Figure 11:
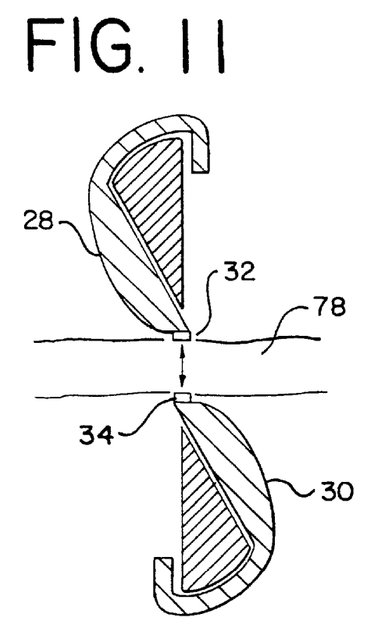
FIG. 11 is a cross-sectional view of a pair of bipolar electrosurgical scissor blades similar to that shown in FIGS. 10a–c and having an alternate configuration for the cartridge that allows for an offset electrode.

Referring to FIG. 11, an alternate arrangement of the cartridge and electrode combination of FIGS. 10a–c is shown which increases the coaptation of the tissue. This is accomplished by having the electrodes 32, 34 located substantially between the cutting edges of the blade members so that when the tissue 78 is contacted, the electrodes 32, 34 are directly across the tissue 78 from each other, thus minimizing the distance of the current path between the electrodes 32, 34 on the opposite cartridges.

Figure 12:
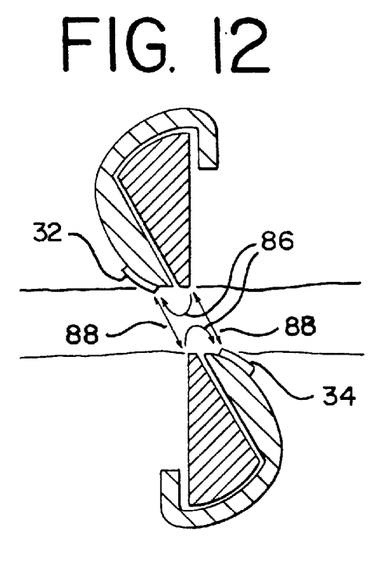
FIG. 12 is a cross-sectional view of a pair of bipolar electrosurgical scissor blades similar in construction to that shown in FIGS. 10a–c and 11, however, the cartridge electrodes are of the same polarity and the blade members are of the opposite polarity.

FIG. 12 shows an embodiment similar to that shown in FIGS. 1–7 with the electrodes on each cartridge being of the same polarity and the scissor blades themselves being connected to the bipolar RF energy source and of the opposite polarity. Like the embodiments of FIGS. 10 and 11, the electrodes 32, 34 in FIG. 12 are located on their respective cartridge members 28, 30 adjacent the cutting edge. Thus, bipolar electric energy 86 flows between each cartridge electrode and its associated scissor blade and bipolar electric energy 88 simultaneously flows between each electrode 32, 34 and the opposite scissor blade. Again, the cartridge can be designed as shown in FIG. 11 to optimize the current path distance and allow for optimum tissue coaptation.

Figure 13A:
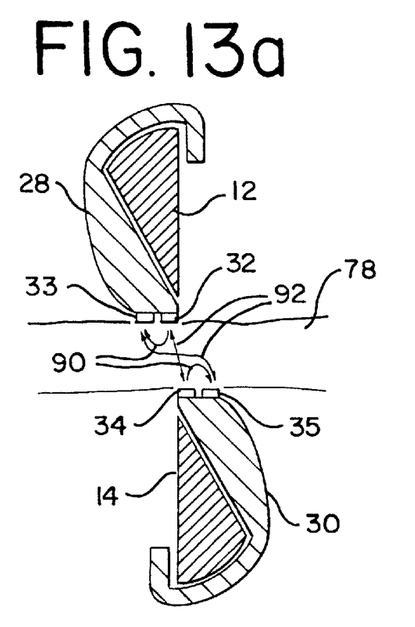
FIGS. 13a–b are cross-sectional views similar to FIGS. 10a–c showing an alternate embodiment of the present invention in which two electrodes are associated with each blade.
Figure 13B:
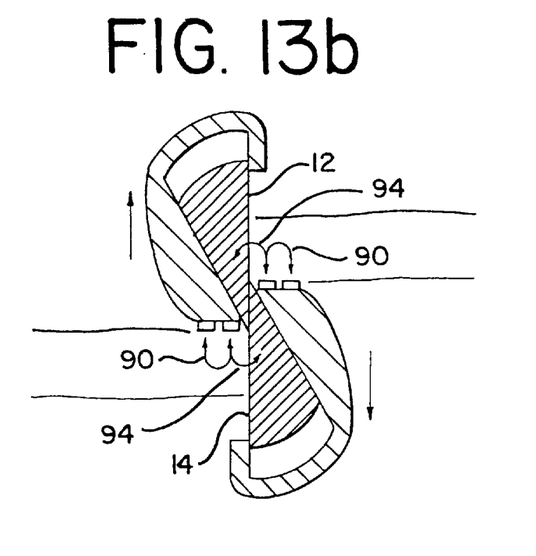

Turning to FIGS. 13a–b, an alternate embodiment of the electrosurgical scissors of the present invention in which each compressible cartridge is shown having dual electrodes. Specifically, cartridge 28 supports electrodes 32, 33, while cartridge 30 supports electrodes 34, 35. As illustrated, the electrodes on each cartridge are of opposite polarity, with electrode 32 on cartridge 28 being of the opposite polarity to that of electrode 34 on cartridge 30. Consequently, when electrodes 32, 33, 34, 35 first contact the tissue 78 (FIG. 13a), current 90 flows through the tissue between the electrodes 32, 33 on cartridge 28 and between electrodes 34, 35 on cartridge 30. Simultaneously, current 92 flows through the tissue between electrodes 32, 34 and between electrodes 33, 35. As the scissors close and the tissue 78 is transected, the scissor blades 12, 14 act as passive electrodes and current 94 will flow between the electrodes on the same cartridge and through the opposite scissor blade (FIG. 13b) from the inner electrode on the opposite cartridge. Simultaneously, current 90 will still flow between the electrodes 32, 33 and between the electrodes 34, 35 through the tissue 78. This and other variations of electrode configuration discussed herein could, of course, be used on the cartridge shown in FIGS. 1–8.

Figure 14A:
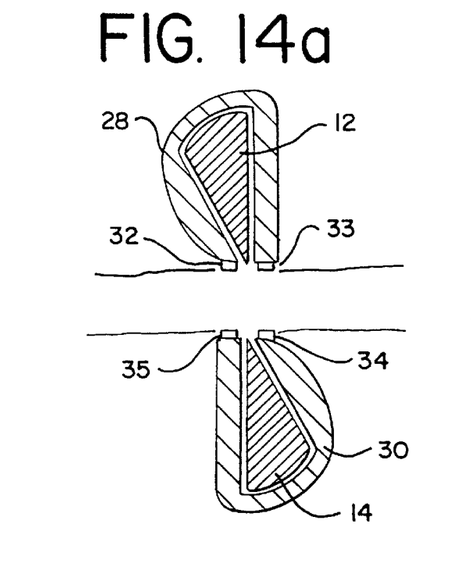
FIGS. 14a–b are cross-sectional views of a further embodiment of the present invention similar to that shown in FIGS. 13a–b in that two electrodes are associated with each blade member.
Figure 14B:
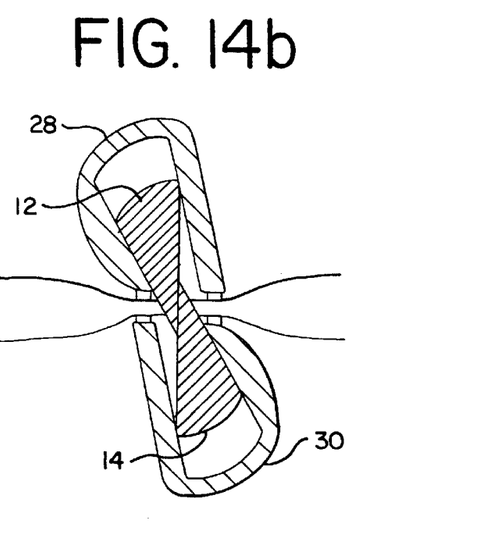

FIGS. 14a–b show an alternate construction of the cartridges 28, 30 in which each cartridge supports two electrodes, 32, 33 and 34, 35, respectively. In this embodiment, each cartridge member 28, 30 substantially surrounds its respective blade member 12, 14, but flexes to permit engagement of the cutting edges and shearing surfaces of the blades when the scissors are closed. This embodiment provides for additional coaptation of the tissue.

Figures 15A, 15B, 15C, 16:
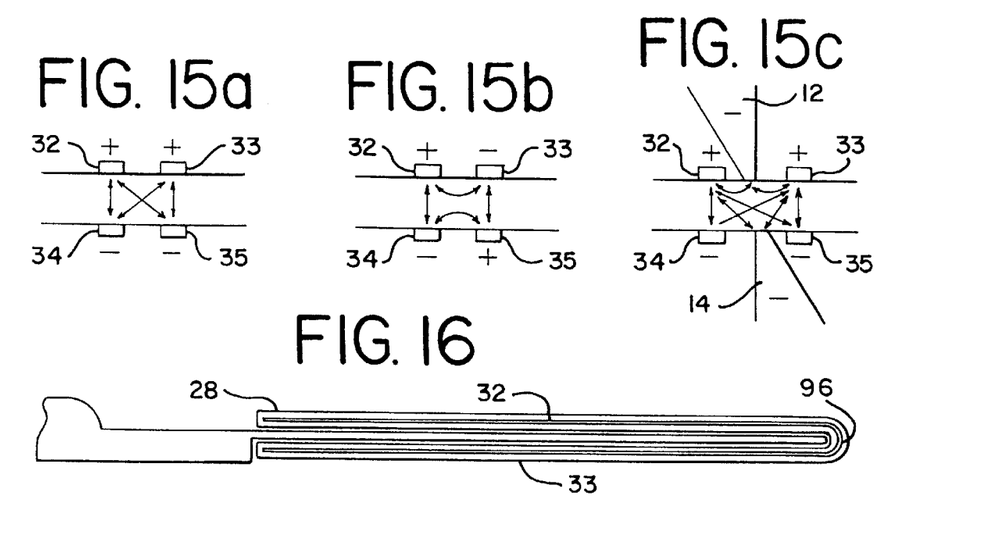
FIGS. 15a–c show various combinations of polarity for the electrodes of the electrosurgical scissors shown in FIGS. 13a–b and 14a–b.
FIG. 16 shows an electrode configuration suitable for the cartridge and electrode combination shown in FIGS. 15a and 15c.

Current flow between the electrodes of FIG. 14 is illustrated in FIGS. 15a–c when the electrodes are variously of the same or opposite polarities. The electrodes associated with each cartridge 28, 30 in FIGS. 14a, 14b can be of the same polarity (FIG. 15a), providing a maximum of current flowing between cartridges, or of opposite polarity (FIG. 15b) which permits current both between the electrodes on the opposite cartridges and between the electrodes on the same cartridge. Alternatively, as shown in FIG. 15c, the electrodes on each cartridge can be of the same polarity (as in FIG. 15a), while the blade members are also charged so that they are of the same polarity thus preventing a short circuit between the blades when their shearing surfaces contact each other. These same electrode polarities could be applied to the design shown in FIG. 13.

Figure 17:
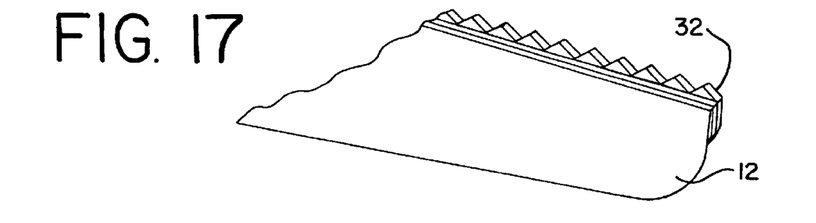
FIG. 17 is a perspective view of a blade member according to the present invention in which the electrode has a sawtooth profile.

If the electrodes on each cartridge are to be of the same polarity (as in FIGS. 15a and 15c), the electrodes can be made of a single piece of conductive material that wraps around the distal end of the cartridge. As illustrated in FIG. 16, electrodes 32, 33, for example, are made of a single piece of conductive material 96 secured to the cartridge 28. Additionally, the tissue engaging surfaces of the electrodes can be formed or shaped to optimize both tissue coagulation and gripping of the tissue. As seen in FIG. 17, the electrode 32 has a sawtooth profile. Optimum tissue gripping is provided by the teeth of the electrode 32 and coagulation is enhanced due to the increased surface area of the electrode 32 (as compared to an electrode having a flat surface).

As can now be readily appreciated, many advantages accrue to the present invention over prior electrosurgical scissors. The removable cartridge/electrode assemblies permit use of a conventional scissors construction that is easily cleaned, sharpened, and resterilized after each use, once the cartridges are removed. Further, the cartridges can be constructed to provide maximum coaptation of the tissue to be cut both before and during the cutting action.

Although the invention has been described in conjunction with various alternative embodiments, there is no intent to limit the invention to these particular versions, and it is contemplated that other cartridge configurations may be used embodying the present invention which depart from the construction shown in the figures.

We claim:

1. An electrosurgical instrument comprising:
    first and second permanent blade members, each blade member having a tissue engaging surface;
    said blade members being relatively movable between open and closed positions;
    a cartridge member removably carried by one of said blade members, said cartridge including a tissue engaging surface for engaging tissue positioned between said blade members as said blade members move toward their closed position;
    said tissue engaging surface of said cartridge member including an electrode, said cartridge member further comprising an electrically insulative material insulating said electrode from said blade member carrying said cartridge member;
    first and second electrical conductors connected respectively to said electrode and to a selected one of said blade members, for communication with the terminals of an RF power supply.

2. The instrument of claim 1 in which said blade members include a shearing surface and cutting edge, and said blade members are of an electrically conductive material.

3. The instrument of claim 2 in which said electrode is elongated and extends substantially parallel to said cutting edge.

4. The instrument of claim 2 in which at least one of said blade members includes an elongated tissue contacting surface that extends generally parallel to said cutting edge.

5. The instrument of claim 4 in which said tissue contacting surface of said cartridge member is generally parallel and coplanar to said tissue contacting surface of at least one said blade member.

6. The instrument of claim 2 in which said tissue engaging surface of said cartridge member is between the cutting edge of its associated blade member and the other of said blade members when said blade members are in the open position so that as the blades move toward the closed position with tissue positioned between said blade members, the tissue engaging surface of said cartridge engages the tissue before the tissue is contacted by the cutting edges of said blade members.

7. The instrument of claim 2 in which said cartridge member includes a base portion and said electrode member is carried by said base portion.

8. The instrument of claim 7 in which said blade member carrying said cartridge member includes an outer surface facing generally opposite said shearing surface and said cartridge is mounted on said outer surface of said blade member with said insulative material disposed between said blade member and said electrode.

9. The instrument of claim 2 wherein said cartridge member permits relative movement between said electrode and said cutting edge of the blade member on which it is carried between a first position when said blade members are open in which said first electrode is located between the cutting edges of said blade members and a second retracted position in which said electrode is located substantially parallel to or behind the cutting edge of the respective blade member when said blade members are closed on tissue to be cut so as not to interfere with the cutting action of said blade members.

10. The instrument of claim 9 in which said cartridge member is secured to its blade member so as to permit relative movement between said electrode and its associated blade member as the blade members close on tissue being cut.

11. The instrument of claim 9 wherein said cartridge member is sufficiently flexible material so that the relative movement between said first electrode and cutting edge of said first blade member is achieved by flexing of said cartridge member as the blade members close on tissue being cut.

12. The instrument of claim 1 in which each of said first and second blade members removably carries one of said cartridge members and each of said blade members includes an electrically conductive shearing surface and cutting edge.

13. The instrument of claim 1 in which said cartridge member includes at least two electrically insulated electrodes, one of said electrodes communicating with said first conductor and the other of said electrodes communicating with said second conductor.

14. The instrument of claim 1 in which said cartridge member is resilient and removably carried on said blade member by an interference fit between said cartridge member and said blade member.

15. The instrument of claim 14 in which selected of said cartridge member and said blade member on which it is carried includes pins for removably engaging the other of said cartridge member and said blade member to form said interference fit.

16. The instrument of claim 14 in which selected of said cartridge member and said blade member on which it is carried includes a projecting stem having an enlarged end portion and the other of said cartridge member and said blade member includes a slot for removably receiving and retaining said enlarged end portion to form said interference fit.

17. The instrument of claim 1 wherein selected of said cartridge member and blade member include interfitting projections and the other of said cartridge member and blade member includes recesses for receiving said projections to secure said cartridge member to said blade member.

18. The instrument of claim 1 wherein a second cartridge member and electrode is removably carried by the other of said blade members and said first electrical conductor is connected to said electrode and said second electrical conductor is connected to said blade member.

19. The combination of claim 1 wherein a second cartridge member and electrode is removably carried by the other of said blade members and said second electrical conductor is connected to said second electrode.

20. A cartridge for removable attachment to a permanent blade of surgical scissors, said cartridge comprising:

a base portion and at least one electrode carried on said base portion;

a tissue contacting surface disposed so that when the cartridge is mounted on a scissor blade, the tissue contacting surface will contact the tissue being cut as the scissor blades close on it;

said electrode defining at least a portion of said tissue contacting surface of said cartridge; and said base portion comprising an electrically insulative material for insulating said electrode from the blade of a scissors when mounted thereon.

21. The cartridge of claim 20 wherein said cartridge includes two electrodes defining at least a portion of said tissue contacting surface, said electrodes being in electrical communication.

22. The cartridge of claim 20 wherein said cartridge includes two electrodes defining at least a portion of said tissue contacting surface, said electrodes being electrically insulated.

23. The cartridge of claim 20 wherein said electrode is generally elongated to contact tissue along at least a substantial portion of the scissor blade as it closes on tissue being cut.

24. The cartridge of claim 20 in which said base portion is sufficiently resilient for an interference fit with the scissor blade.

25. The cartridge of claim 20 comprising a plurality of resilient engaging members for engaging a scissor blade.

26. The cartridge of claim 25 wherein said engaging members comprises resilient pins.

27. The cartridge of claim 25 wherein said engaging members comprise resilient extensions having enlarged end portions.

28. The cartridge of claim 20 wherein said base portion is essentially entirely of electrically insulative material to insulate said electrode.

29. The cartridge of claim 20 wherein said electrode includes a proximal end, a distal end and an elongated portion therebetween, and said distal end includes a curved nose portion.

30. The cartridge of claim 20 wherein said electrode includes a proximal end, a distal end and an elongated portion therebetween, and said proximal end includes a contact portion for contacting an electrical conductor associated with the scissors.

31. The instrument of claim 1 or 20 in which said electrode includes a gripping surface.

32. The instrument of claim 31 in which the surface of said electrode has a sawtooth profile.

* * * * *